US010617380B2

(12) United States Patent
Tagawa et al.

(10) Patent No.: US 10,617,380 B2
(45) Date of Patent: Apr. 14, 2020

(54) RADIOGRAPHIC IMAGING APPARATUS AND RADIOGRAPHIC IMAGING SYSTEM

(71) Applicant: CANON KABUSHIKI KAISHA, Tokyo (JP)

(72) Inventors: Motoki Tagawa, Chigasaki (JP); Takahiro Koyanagi, Kawasaki (JP); Youjirou Hiratsuka, Yokohama (JP); Satoru Omura, Chigasaki (JP); Katsushi Kato, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 210 days.

(21) Appl. No.: 15/719,196

(22) Filed: Sep. 28, 2017

(65) Prior Publication Data
US 2018/0092618 A1    Apr. 5, 2018

(30) Foreign Application Priority Data

Oct. 5, 2016  (JP) ................. 2016-196896
Nov. 24, 2016 (JP) ................. 2016-228060
Nov. 24, 2016 (JP) ................. 2016-228062

(51) Int. Cl.
*A61B 6/00*    (2006.01)
*H04R 1/02*    (2006.01)

(52) U.S. Cl.
CPC .............. *A61B 6/54* (2013.01); *A61B 6/40* (2013.01); *A61B 6/42* (2013.01); *A61B 6/4283* (2013.01); *A61B 6/46* (2013.01); *A61B 6/461* (2013.01); *H04R 1/023* (2013.01); *H04R 1/028* (2013.01); *H04R 2430/01* (2013.01)

(58) Field of Classification Search
CPC .......... H04R 1/028; A61B 6/4283; A61B 6/54
See application file for complete search history.

(56) References Cited

U.S. PATENT DOCUMENTS

| 7,751,696 B2 | 7/2010 | Tatamiya | |
|---|---|---|---|
| 2008/0296507 A1* | 12/2008 | Petrick | G01T 1/247 250/370.09 |
| 2010/0054399 A1* | 3/2010 | Nishino | A61B 6/4233 378/28 |
| 2014/0027636 A1* | 1/2014 | Watano | G01T 1/16 250/336.1 |

FOREIGN PATENT DOCUMENTS

| JP | 2005-013272 A | 1/2005 |
|---|---|---|
| JP | 2011-232693 A | 11/2011 |
| JP | 2012-100962 A | 5/2012 |
| JP | 2012-186549 A | 9/2012 |

* cited by examiner

*Primary Examiner* — Yara B Green
(74) *Attorney, Agent, or Firm* — Canon USA, Inc., IP Division

(57) ABSTRACT

A radiographic imaging apparatus includes a sensor panel, a sound emitting member that provides notification of a state via sound, a casing that contains the sensor panel and the sound emitting member, where the casing includes a first sound transmission hole and a sound transmission member that covers the first sound transmission hole, where the sound transmission member includes a second sound transmission hole with a smaller diameter than a diameter of the first sound transmission hole. The radiographic imaging apparatus includes a detection unit that detects information related to an installed state of the radiographic imaging apparatus and a control unit that controls a volume of the emitted sound based on the detected information.

33 Claims, 15 Drawing Sheets

FIG.12

| IMAGING PORTION | VOLUME PARAMETER |
|---|---|
| HEAD | 1 |
| SHOULDER | 2 |
| CHEST | 3 |
| SPINE | 3 |
| ARM | 3 |
| ABDOMEN | 4 |
| LUMBER VERTEBRA | 4 |
| LOWER BODY | 5 |

FIG.15

| IMAGING PORTION | VOLUME PARAMETER | | |
|---|---|---|---|
| | P0 | P1 | P2 |
| HEAD | 1 | 2 | 3 |
| NECK/SHOULDER | 2 | 3 | 4 |
| CHEST | 3 | 4 | 5 |
| SPINE | 3 | 4 | 5 |
| ARM | 3 | 4 | 5 |
| ABDOMEN | 4 | 5 | 5 |
| LUMBER VERTEBRA | 4 | 5 | 5 |
| LOWER BODY | 5 | 5 | 5 |

RADIOGRAPHIC IMAGING APPARATUS AND RADIOGRAPHIC IMAGING SYSTEM

BACKGROUND

Field

The present disclosure relates to a radiographic imaging apparatus that captures a radiographic image and to a radiographic imaging system using the radiographic imaging apparatus.

Description of the Related Art

Recently, radiographic imaging apparatuses using a semiconductor sensor to capture a digital image have been used to capture radiographic images used for medical imaging diagnosis and non-destructive examination. Differing from conventional imaging using a photosensitive film, imaging with such an apparatus enables a user to immediately check captured radiographic images, which has remarkably improved work efficiency.

Some radiographic imaging apparatuses can include a notification unit that notifies a user of a state of the apparatus so that imaging can be more conveniently performed. Japanese Patent Application Laid-Open No. 2005-013272 discusses an X-ray imaging apparatus that notifies a user of a driving state of an X-ray detector with light or sound. Japanese Patent Application Laid-Open No. 2012-100962 discusses a radiographic image detection apparatus that includes electronic cassettes provided with a speaker, and controls sound output based on which of the electronic cassettes is selected to be used for imaging.

Radiographic imaging apparatuses can be exposed to liquids, such as when a radiographic imaging apparatus is cleaned with water, an antiseptic solution, or the like. When the radiographic imaging apparatus includes a sound transmission hole through which sound from a sound emitting member in the radiographic imaging apparatus is output, this can result in the radiographic imaging apparatus being damaged should liquid enter through the sound transmission hole.

When the radiographic imaging apparatus includes a speaker as the sound emitting member to issue notifications, sound can be blocked with the speaker being muffled depending on an arrangement of the speaker and a use environment of the radiographic imaging apparatus, resulting in a failure of an operator to hear the sound. In a configuration where the operator performs an operation at a location distant from a subject, or in a room, e.g., a console room, different from an examination room, the notification is preferably performed with notification sound with a certain volume. However, large sound emitted from the radiographic imaging apparatus can be irritating for the subject near the apparatus or can actually have a negative health effect on the ears of the subject, depending on an imaging condition.

SUMMARY OF THE INVENTION

The present disclosure is directed to enabling a radiographic imaging apparatus, having a notification function based on sound, to have a higher waterproof performance and to issue notification to an operator with sound with an appropriate volume, regardless of the use environment or an installed state of the apparatus.

According to an aspect of the present disclosure, a radiographic imaging apparatus includes a sensor panel configured to convert radiation into an image signal, a sound emitting member configured to provide notification of a state of the radiographic imaging apparatus via sound, a casing configured to contain the sensor panel and the sound emitting member, the casing including a first sound transmission hole, and a sound transmission member configured to cover the first sound transmission hole, the sound transmission member including a second sound transmission hole with a smaller diameter than a diameter of the first sound transmission hole.

According to another aspect of the present disclosure, a radiographic imaging apparatus include a radiation detection unit configured to convert radiation transmitted through a subject into an electrical signal, a sound emitting unit configured to emit sound for notification, a detection unit configured to detect information related to an installed state of the radiographic imaging apparatus, and a control unit configured to control a volume of the emitted sound based on the detected information.

According to yet another aspect of the present disclosure, a radiographic imaging system includes a radiographic imaging apparatus including a radiation detection unit configured to convert radiation transmitted through a subject into an electrical signal and a sound emitting unit configured to emit sound for notification, an acquisition unit configured to acquire information related to an imaging condition, and a setting unit configured to set a volume of the emitted sound based on the information related to the imaging condition.

With the present disclosure, a radiographic imaging apparatus including a notification function using sound can notify an operator of a state of the apparatus with sound with an appropriate volume, regardless of a use environment or an installed state of the apparatus.

Further features will become apparent from the following description of exemplary embodiments with reference to the attached drawings.

BRIEF DESCRIPTION OF THE DRAWINGS

FIG. 12 is a diagram illustrating an example of a lookup table according to the sixth exemplary embodiment.

FIG. 15 is a flowchart illustrating a lookup table according to a seventh exemplary embodiment.

DESCRIPTION OF THE EMBODIMENTS

Exemplary embodiments are described below with reference to the drawings. Radiation is an X-ray in the exemplary embodiments, but can also be an α-ray, a β-ray, a γ-ray, a corpuscular ray, a cosmic ray, or the like.

Figure 1:
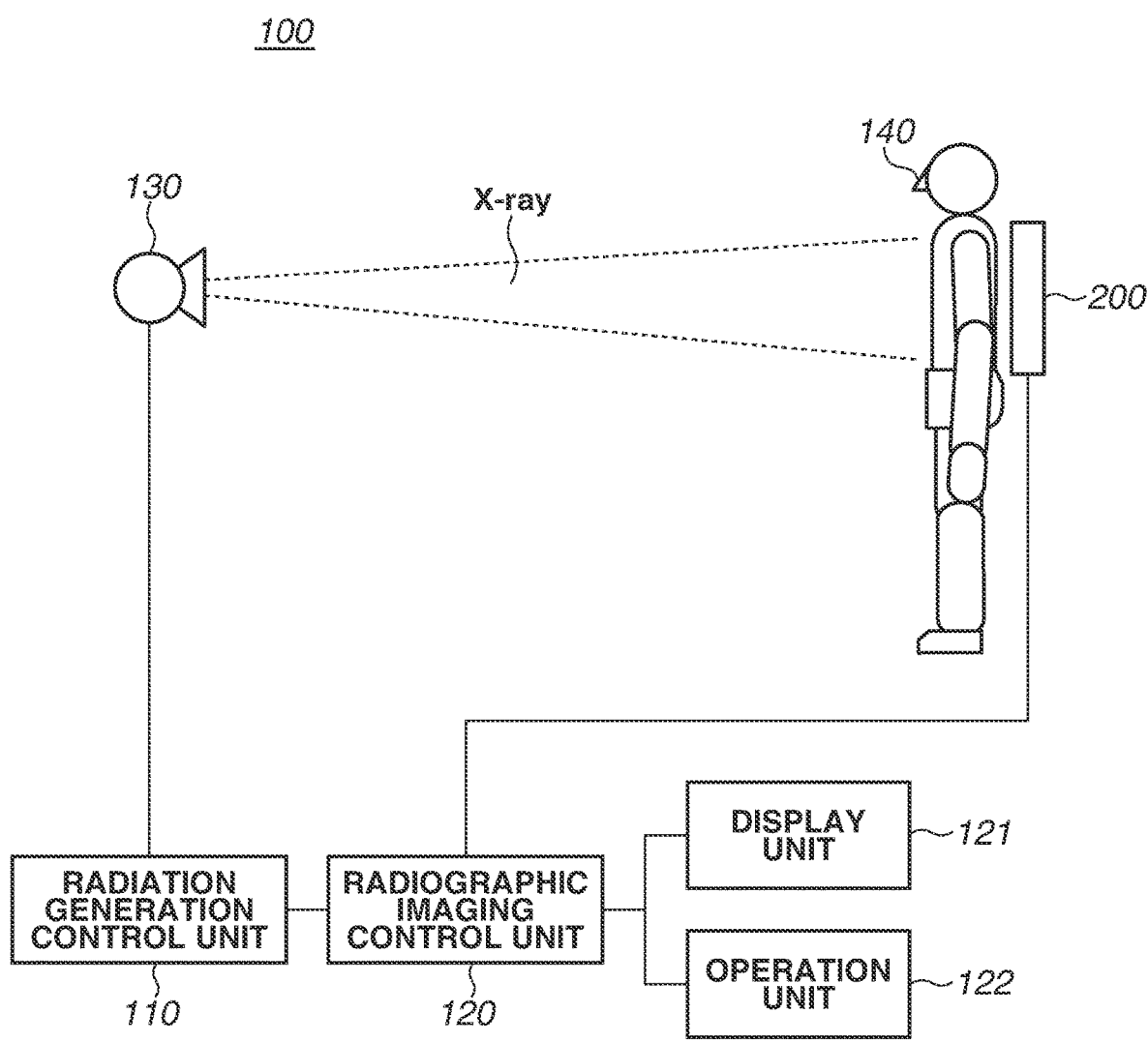
FIG. 1 is a schematic view of a radiographic imaging system according to a first exemplary embodiment.

A radiographic imaging system according to a first exemplary embodiment is described with reference to FIG. 1. A radiographic imaging system (hereinafter, referred to as an imaging system) 100 performs examination (imaging) based on an examination order including a plurality of pieces of examination information, and acquires a radiographic digital image (hereinafter, referred to as a radiographic image). The examination information includes imaging protocol information. The imaging protocol information includes parameter information or imaging execution information used for imaging, image processing, or the like, and includes imaging environment information indicating a type of a sensor and a posture during the imaging. The examination information includes information for determining an examination order such as an examination ID or a reception number and information for determining a radiographic image corresponding to the examination order.

A radiation source 130 functions as a radiation generation unit including an X-ray tube, and irradiates a subject (examinee) 140 with an X-ray.

A radiation generation control unit (hereinafter, referred to as a generation control unit) 110 controls generation of radiation based on an imaging protocol and is controlled by a radiographic imaging control unit (hereinafter, referred to as an imaging control unit) 120. More specifically, the generation control unit 110 causes the radiation source 130 to generate radiation by applying voltage to the radiation source 130 based on an imaging condition, e.g., a parameter such as tube current, tube voltage, and irradiation time, corresponding to the imaging protocol.

The imaging control unit 120 performs overall control on radiographic imaging processing based on the imaging protocol. The imaging control unit 120 executes image processing on a radiographic image acquired from a radiographic imaging apparatus (hereinafter, referred to as an imaging apparatus) 200. The imaging processing includes gradation processing and frequency processing, and is executed with an image processing parameter based on the imaging protocol. The imaging control unit 120 is, for example, hardware such as a personal computer (PC), a central processing unit (CPU), or a field programmable gate array (FPGA).

A display unit 121 is, for example, a display, and displays information on a system state and a radiographic image to an operator. The display unit 121 can display an examination order received external from the imaging apparatus 200 or generated by the operator of the imaging apparatus 200. An operation unit 122 receives an instruction from the operator. Examples of the operation unit 122 include a keyboard, a mouse, and various buttons. The operator can input an operation instruction to the imaging apparatus 200 via the operation unit 122.

The imaging apparatus 200 detects electric charges corresponding to an amount of radiation transmitted through the subject 140, generates image data, and transfers the image data to the imaging control unit 120.

Figure 2A:
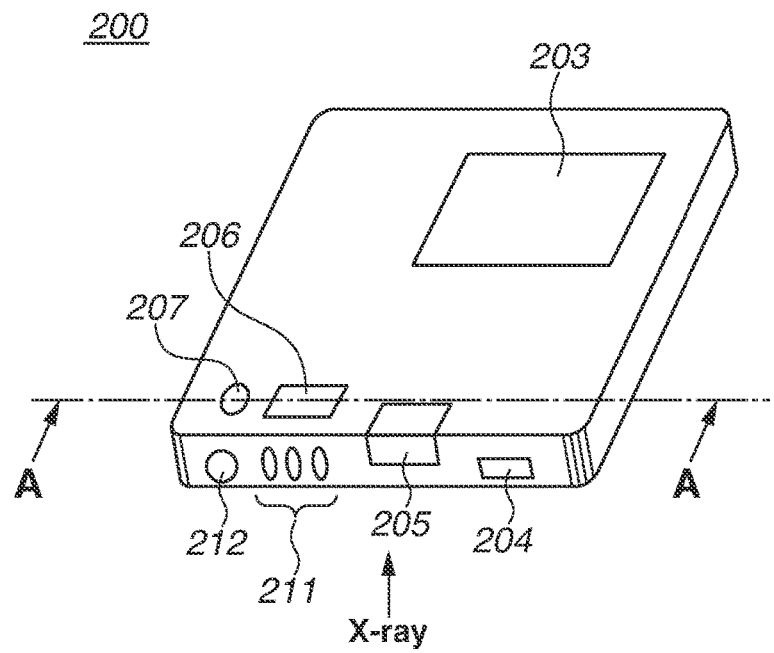
FIGS. 2A and 2B are an outer view and a block diagram of a radiographic imaging apparatus according to the first exemplary embodiment and a fourth exemplary embodiment.
Figure 2B:
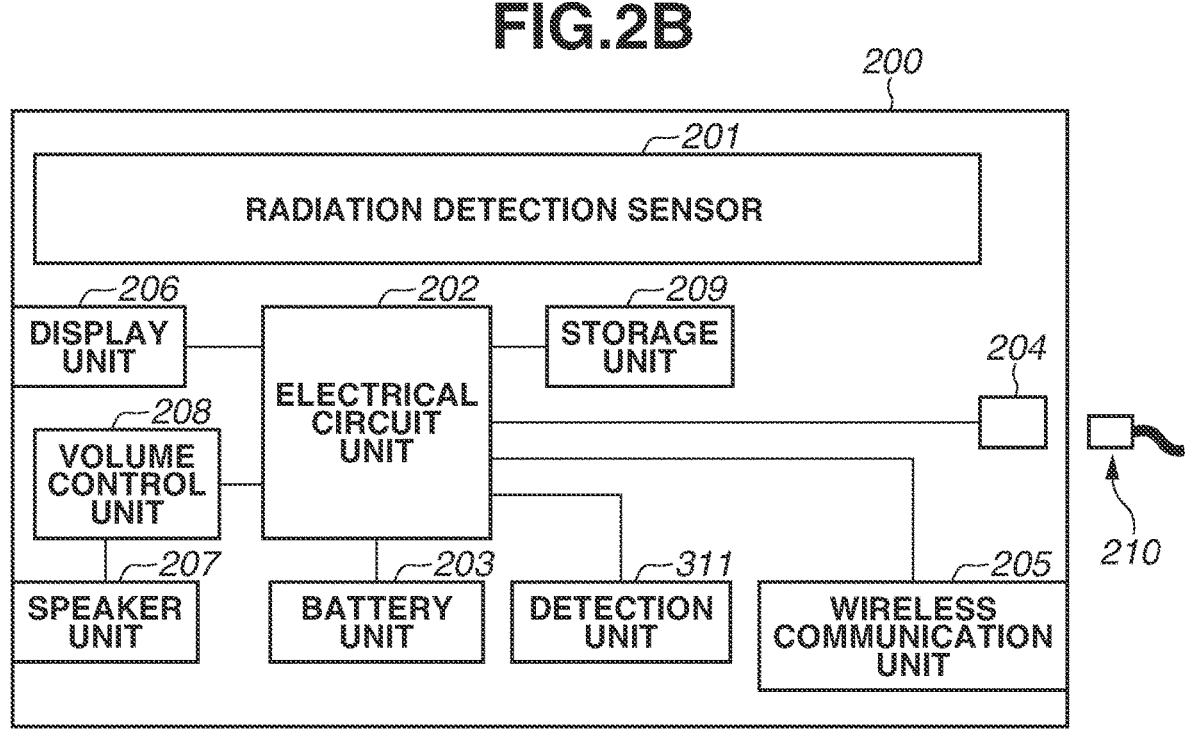
Figure 3:
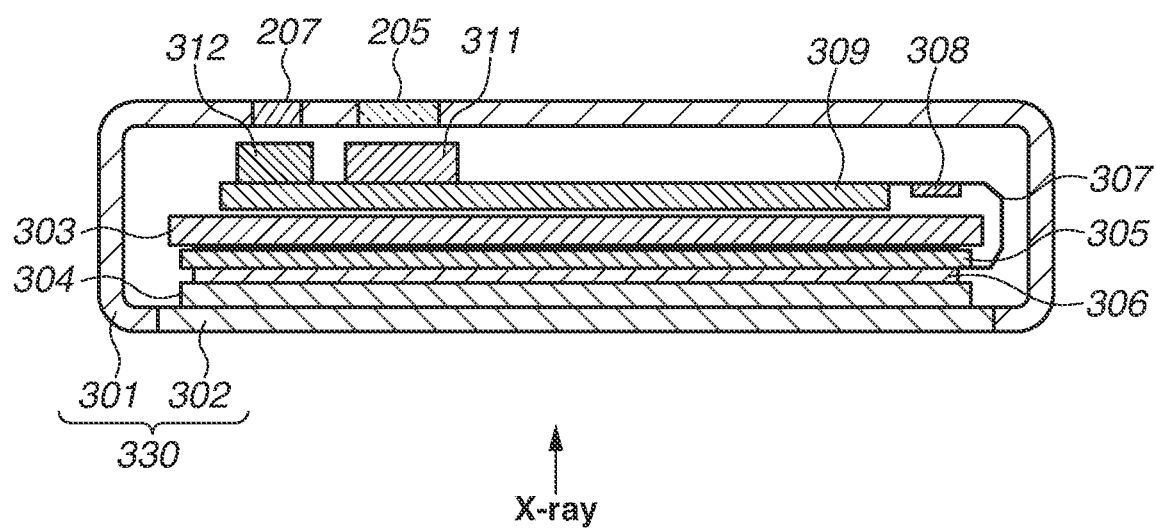
FIG. 3 is a cross-sectional view of the radiographic imaging apparatus according to the first exemplary embodiment and the fourth exemplary embodiment.

Next, the imaging apparatus 200 is described with reference to FIGS. 2A and 2B and FIG. 3. FIG. 2A is a perspective view of the imaging apparatus 200 as viewed in a direction toward a surface (rear surface) opposite to a radiation irradiation surface. FIG. 2B is a block diagram illustrating functional blocks of the imaging apparatus 200. FIG. 3 is a cross-sectional view taken along the line A-A in FIG. 2A.

The imaging apparatus 200 executes imaging processing with power supplied from a battery unit 203 detachably held on the rear surface. The imaging apparatus 200 can wirelessly communicate with the imaging control unit 120 with a wireless communication unit 205. The battery unit 203 can be replaced when the remaining battery charge is low, etc. When a wireless connection is unstable, the user can connect a cable (not illustrated) to a wired communication connection portion 204 so that wired power supply and wired communications can be implemented.

A switch 212 is used for performing an operation for turning ON and OFF the imaging apparatus 200, and an operation for switching between a state where the imaging can be executed and cannot be executed and the like. A state display unit 211 displays light of various colors in a flashing or blinking manner or turns off the light to indicate that the power is ON/OFF, or to indicate the remaining battery charge of the battery unit 203 or the like.

The imaging apparatus 200 has a rear surface provided with a display unit 206 that displays information such as imaging patient information, an imaging condition, and the number of images that can be captured. This is because the imaging apparatus 200 has a thickness of approximately 15 mm, and thus it is difficult to display a large variety of information on the state display unit 211.

A sound transmission unit (speaker unit) 207 has a function of issuing notification of a state of the imaging apparatus 200 via sound. For example, with the sound transmission unit 207, the state of the imaging apparatus 200 can be recognized even in a situation where the display unit 206 is difficult to visually recognize, such as, for example, a situation where the imaging apparatus 200 is disposed below the patient. The switch 212, the state display unit 211, the display unit 206, and the sound transmission unit 207 are disposed in an area where a front surface and a side surface of a casing 330 are adjacent to each other. Thus, the user can perform an operation by easily recognizing the state without largely moving the user's line of sight.

The imaging apparatus 200 incorporates a sensor panel 305 obtained by forming a photoelectrical conversion element on a glass substrate. The sensor panel 305 includes a scintillator 306 that converts radiation into visible light, and is formed on a surface provided with the photoelectrical conversion element. CsI or the like is preferably used for the scintillator 306. The scintillator 306 emits light when the imaging apparatus 200 is irradiated with radiation. The photoelectrical conversion element of the sensor panel 305 converts the light into an electrical signal. The imaging apparatus 200 generates a radiographic image by using the electrical signal. The sensor panel 305 can be a direct conversion type sensor employing a-Se that directly converts the radiation into electric charges.

The electrical signal generated by the sensor panel 305 is transmitted to an integrated circuit 308 through a flexible substrate 307. The integrated circuit 308 amplifies and performs analog-to-digital (A/D) conversion on the electrical signal to generate a digital image signal (image signal). The image signal is further processed in an electrical circuit board 309 and then is transferred to the imaging control unit 120.

The sensor panel 305 can include a radiation irradiation detection function. With the radiation irradiation detection function, the imaging apparatus 200 determines that the sensor panel 305 is irradiated with radiation and starts an image processing operation. In the present exemplary embodiment, a radiation irradiation signal generated by the sensor panel 305 in response to the radiation irradiation is read, and the sensor panel 305 is determined to be irradiated with radiation when a value of the signal is greater than or equal to a threshold. The radiation irradiation signal is an electrical signal, and is amplified and subjected to the A/D conversion by the integrated circuit 308 or by another circuit (not illustrated) mounted on the electrical circuit board 309. The electrical circuit board 309 determines whether the digital signal has a value that is greater than or equal to the threshold. Thus, the radiation irradiation detection function is implemented.

The sensor panel 305 includes a supporting plate 303 fixed on a surface opposite to the radiation irradiation surface, so as not to deform or crack due to an external load, vibrations during transportation, or the like. Carbon Fiber Reinforced Plastic (CFRP), a magnesium alloy, an aluminum alloy, and the like are used for the supporting plate 303, so that both strength and light weight can be achieved. The supporting plate 303 also includes a radiation shielding member that prevents the electrical circuit board 309 from deteriorating due to radiation, removing scattering rays from the rear surface of the imaging apparatus 200, or the like. For example, a material with a high specific gravity such as molybdenum, iron, and lead is used for the radiation shielding member. The casing 330 defines an outer wall of the imaging apparatus 200. The casing 330 includes a radiotransparent plate 302 and a main body portion 301. The radiotransparent plate 302 is provided on the radiation irradiation surface. The main body portion 301 is a portion of the casing 330 other than the radiotransparent plate 302. The main body portion 301 contains the sensor panel 305 and a sound emitting member 312. CFRP is preferably used for the radiotransparent plate 302, so that both radiotransparency and rigidity can be achieved. CFRP, a magnesium alloy, an aluminum alloy, and the like are preferably used for the main body portion 301, so that both strength and light weight can be achieved. A buffer material 304 is disposed between the radiotransparent plate 302 and an internal component. The buffer material 304 can provide an external load distributing effect and a shock absorbing effect for the imaging apparatus 200. For example, the buffer material 304 is obtained by packing a silicone or urethane foaming material, silicone gel, elastomer, and gas in an air sac. The sensor panel 305, the supporting plate 303, and the buffer material 304 form a radiation detection sensor 201.

The sound emitting member 312 and a light emitting member 311 are mounted on the electrical circuit board 309. The sound emitting member 312 is, for example, a speaker that can emit sound based on an electrical signal. Examples of the light emitting member 311 include a liquid crystal display, an organic electroluminescence (EL) display, and a 7-segment light emitting diode (LED). The main body portion 301 has a portion facing the light emitting member 311 provided with an opening, and a transparent member is attached to cover the opening. A sound transmission hole (opening) is formed in a portion of the main body portion 301 facing the sound emitting member 312.

Figure 4:
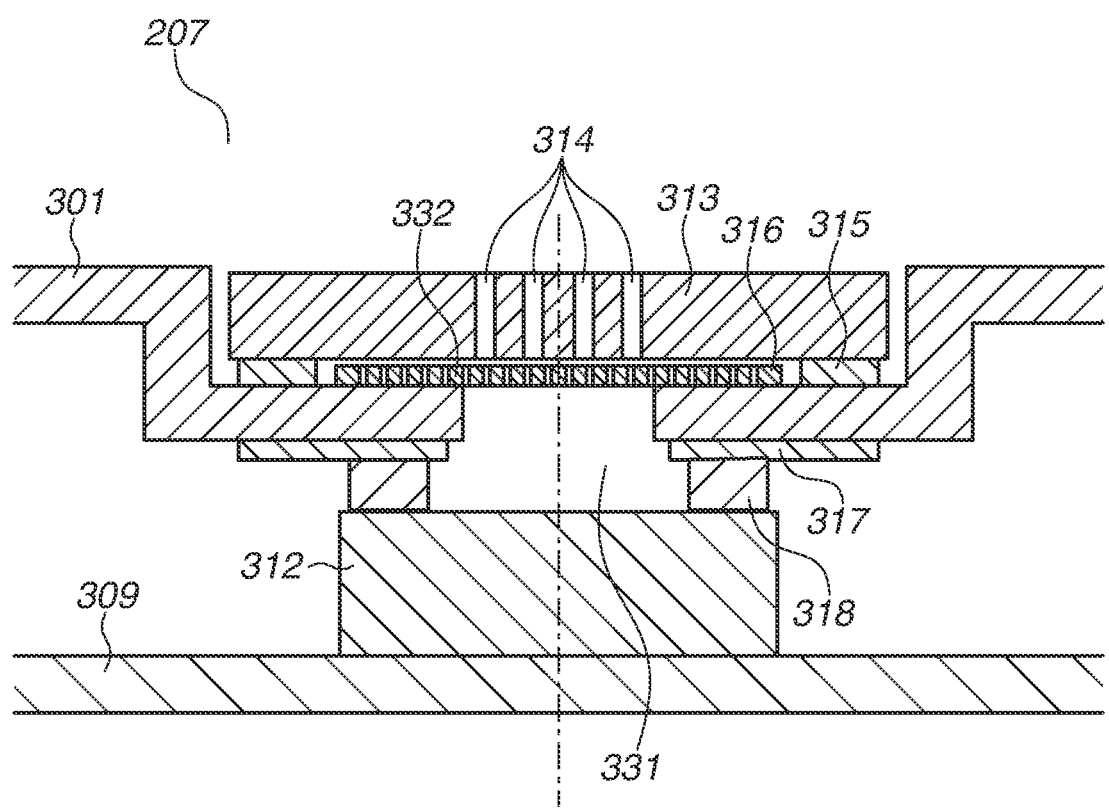
FIG. 4 is a cross-sectional view of a portion around a sound transmission unit in the radiographic imaging apparatus according to the first exemplary embodiment.

The sound transmission unit 207 is described in detail with reference to FIG. 4. A sound transmission hole (first sound transmission hole 331) having a diameter of 3 to 10 mm is formed in the portion of the main body portion 301 facing the sound emitting member 312. A sound transmission member 316 is adhered to cover the first sound transmission hole 331.

The sound transmission member 316 is provided with a plurality of openings (second sound transmission holes 332) so that an attempt to prevent attenuation of the sound emitted from the sound emitting member 312 is facilitated. The second sound transmission holes 332 each have a diameter that is less than or equal to 1 mm. The volume of the sound emitted from the sound emitting member 312 is set to be higher than the volume of the notification sound heard by the operator, considering the attenuation in the sound transmission unit 207. The sound transmission member 316 has the second sound transmission holes 332 so that an attempt to prevent the attenuation of the sound in the sound transmission unit 207 can be facilitated. Thus, in the imaging apparatus 200, the attenuation can be compensated with a minimum possible increased amount of the volume of the sound emitted from the sound emitting member 312. Thus, in the imaging apparatus 200, the electromagnetic waves generated by the sound emitting member 312 can be reduced as much as possible, whereby image noise and false detection can be prevented.

The second sound transmission hole 332 has a diameter small enough to be liquid impermeable so that liquid, such as water, does not enter the imaging apparatus 200 through the second sound transmission hole 332. More specifically, the second sound transmission hole 332 has a diameter smaller than that of the first sound transmission hole 331. Thus, the second sound transmission hole 332 has a higher water stopping performance than the first sound transmission hole 331. The diameter of the second sound transmission hole 332 is determined in accordance with the surface tension of water or the like. Thus, for example, a porous material with a relatively high water repellency such as polytetrafluoroethylene (PTFE) is used for the sound transmission member 316. A higher waterproof performance can be achieved when a material having a relatively high oil repellency is used for the sound transmission member 316. The sound transmission member 316 is preferably fixed on an outer wall side of the main body portion 301 to cover the first sound transmission hole 331 so as to be easily replaceable upon being damaged. Alternatively, the sound transmission member 316 can be fixed on an inner wall side of the main body portion 301 to cover the first sound transmission hole 331.

A cover member 313 is adhered to the outer side of the sound transmission member 316 with a waterproof double sided adhesive tape 315, to cover the first sound transmission hole 331. A third sound transmission hole 314 is formed in the cover member 313 and has a diameter smaller than that of a possible load applying object, e.g., a user's finger tip). The diameter is, for example, approximately 0.1 to 3 mm, and is smaller than that of an air hole formed in the main body portion 301. Thus, the third sound transmission hole has a diameter that is smaller than that of the first sound transmission hole 331 and larger than that of the second sound transmission hole 332.

The sound transmission member 316 can be disposed on an inner side of the main body portion 301 with the air hole having a diameter smaller than that of the possible load applying object, e.g., a user's finger tip, so that a waterproof filter can be prevented from being damaged. In this configuration, the sound transmission member 316 can be prevented from directly receiving a load. A minute hole with a diameter of approximately 1 mm is not suitable for the main body portion 301 made of CFRP. This is because such a hole is likely to cause burring of carbon fibers of CFRP, and thus is difficult to form in the main body portion 301. The minute hole is also not suitable for the main body portion 301 made of a magnesium alloy or the like. This is because forming the minute hole in such a main body portion 301 involves a cumbersome procedure considering the deformation due to the processing and a processing time. Thus, the imaging apparatus 200 includes the cover member 313 to achieve a higher strength and waterproof property for the sound transmission member 316. The imaging apparatus 200 is preferably provided with a plurality of the third sound transmission holes 314 so that sound transmission is facilitated. A resin material or a thin metal material featuring a high workability is used for the cover member 313. Thus, the cover member 313 can be protected without a cumbersome process performed on the main body portion 301. The third sound transmission holes 314 can be inclined relative to the outer wall of the imaging apparatus 200. In the imaging apparatus 200 with such a configuration, the load is less likely to be applied to the sound transmission member 316 through the holes.

The imaging apparatus 200 also includes a sound-shielding gasket 318 and a conductive sheet 317 disposed between the sound emitting member 312 and the main body portion 301. The gasket 318 can prevent the sound emitted from the sound emitting member 312 from spreading into the main body portion 301, so that the sound can be efficiently transmitted external to the casing 330. When the sound transmission member 316 breaks, the gasket 318 can fill the gap between the main body portion 301 and the sound emitting member 312, so that a water entering area can be made small.

The conductive sheet 317 is, for example, a copper foil tape material. The conductive sheet 317 is electrically fixed to the ground. Thus, externally originated noise (static electricity) applied to the sound transmission unit 207 flows to the ground through the conductive sheet 317. As a result, the conductive sheet 317 prevents the static electricity from entering the electrical circuit board 309 through the sound emitting member 312. This is particularly effective when the casing 330 is made of a non-conductive material.

The first sound transmission hole 331 formed in the casing 330 can be sealed airtight with a thin film material having no second sound transmission hole, so that the waterproof performance can be guaranteed. However, in this configuration, sound emitted from the sound emitting member is attenuated to be difficult to be heard by the user. The volume of the sound emitted from the sound emitting member 312 can be increased to compensate for this sound attenuation, but this results in the sound emitting member 312 emitting intense electromagnetic waves to be a heat and noise generating source. In such a case, noise can be superimposed on a captured image and a detection signal for detecting radiation irradiation.

In the present exemplary embodiment, in the imaging apparatus including the state notification function based on sound, image noise or false detection can be prevented while guaranteeing the waterproof performance.

A second exemplary embodiment is described with reference to FIGS. 5, 6A, and 6B. An imaging apparatus 500 according to the present exemplary embodiment includes a plurality of the sound transmission units (speaker units).

Figure 5:
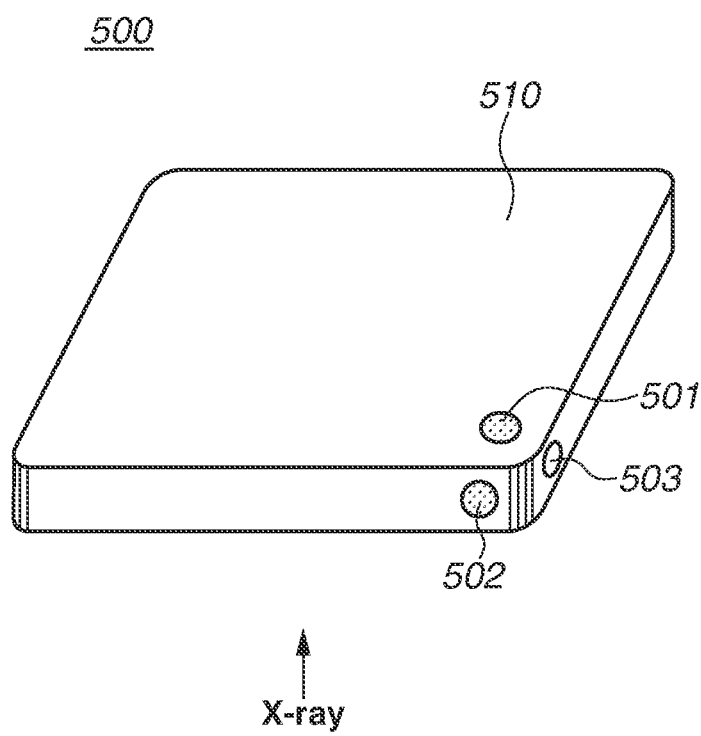
FIG. 5 is an outer view illustrating an arrangement of sound transmission units according to a second exemplary embodiment.

As illustrated in FIG. 5, a casing 510 has a rear surface, a side surface, and another side surface orthogonal to the side surface respectively provided with a rear surface sound transmission unit 501, a first side surface sound transmission unit 502, and a second side surface sound transmission unit 503. Thus, the casing 510 is provided with a plurality of the first sound transmission holes 331 that are provided in at least two surfaces of the casing 510.

The imaging apparatus 500 has the sound transmission units provided in three surfaces of the casing 510, so that at least one sound transmission unit can be exposed even when any two surfaces of the casing 510 are covered. The sound transmission units of the imaging apparatus 500 are disposed close to each other. With such a close arrangement, the imaging apparatus 500 can output the sound from a single sound emitting member (speaker) through a plurality of speaker units in a spreading manner. Furthermore, the sound can be output from one of the plurality of speaker units, with the orientation of the sound emitting member changed in accordance with the orientation and the installed state of the imaging apparatus 500. The imaging apparatus 500 can include the plurality of sound emitting members without having complicated wiring for the sound emitting members in the casing 510.

Figure 6A:
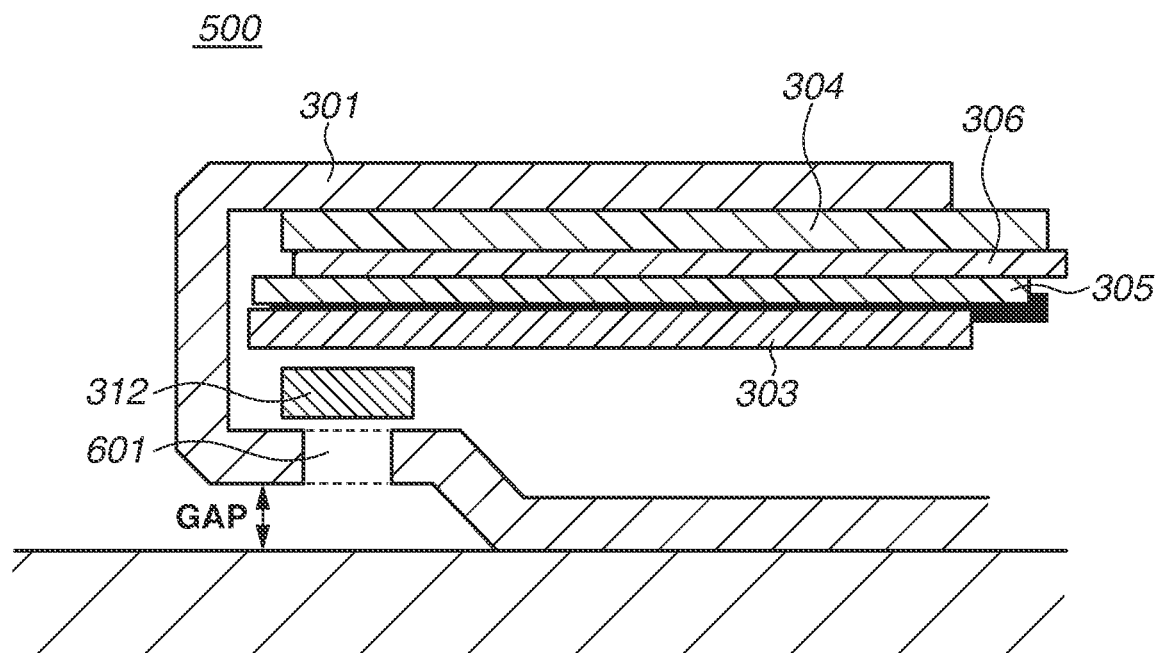
FIGS. 6A and 6B are cross-sectional views each illustrating an arrangement of a sound transmission unit according to the second exemplary embodiment.
Figure 6B:
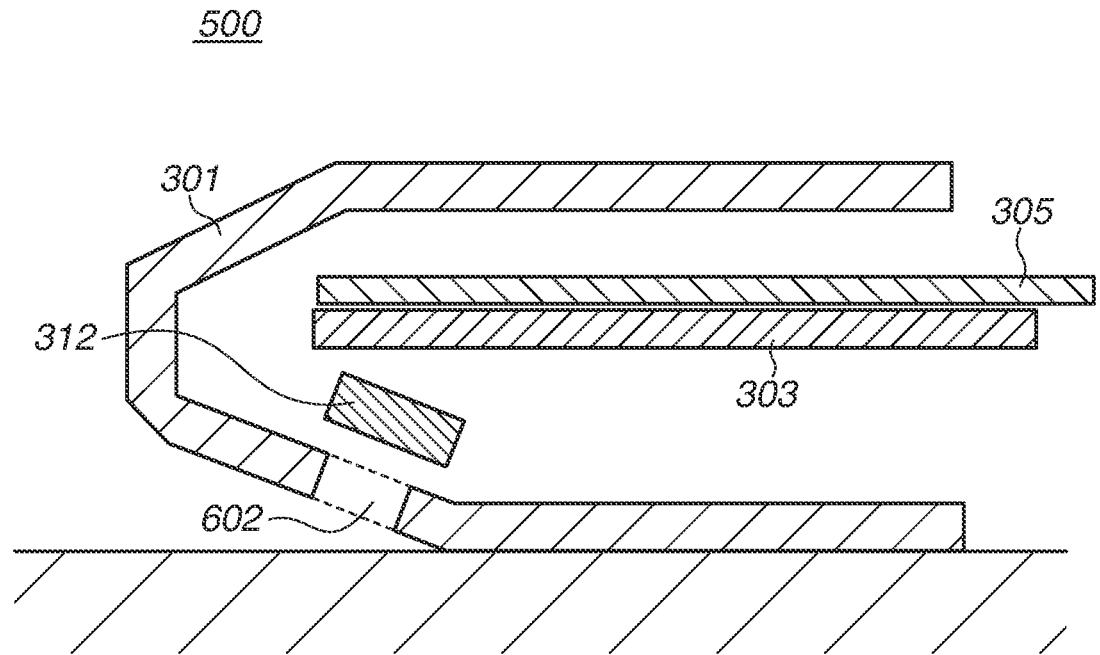

As illustrated in FIGS. 6A and 6B, the imaging apparatus 500 can be configured such that a gap is provided such that only a portion of the main body portion 301 provided with the sound transmission hole 601 is prevented from coming into contact with the floor surface. More specifically, the first sound transmission hole is provided in a position of the casing 510 recessed inward from the outermost shape of the casing 510. With such a shape where the sound emitting member 312 is less likely to be covered with a floor surface or the like, the sound emitted from the sound emitting member 312 in the imaging apparatus 500 can be prevented from being blocked in a situation where a plurality of speaker units is difficult to be provided. As illustrated in FIG. 6A, the portion of the main body portion 301 provided with the sound transmission hole 601 is recessed so as not to come into contact with the floor surface. More specifically, the portion is recessed by 0.1 to 5 mm from the other part of the outer wall. Alternatively, as illustrated in FIG. 6B, the casing 510 can have an inclined portion, between the side and rear surfaces, provided with a sound transmission hole 602.

The imaging apparatus 500 can be installed by the user with the rear surface, opposite to the radiation irradiation surface, or a side surface of the casing 510 facing downward, or with one of the surfaces of the casing 510 in contact with a platform. Also in this situation, the configuration according to the present exemplary embodiment can prevent the volume of the sound from the imaging apparatus 500 to be heard by the user from being low due to the sound transmission unit 207 being blocked. Thus, the imaging apparatus 500 preferably includes a plurality of sound transmission units provided in at least two surfaces of the casing 510.

With the present exemplary embodiment, sound can be prevented from being blocked depending on the orientation and the installed location of the imaging apparatus 500.

Figure 7:
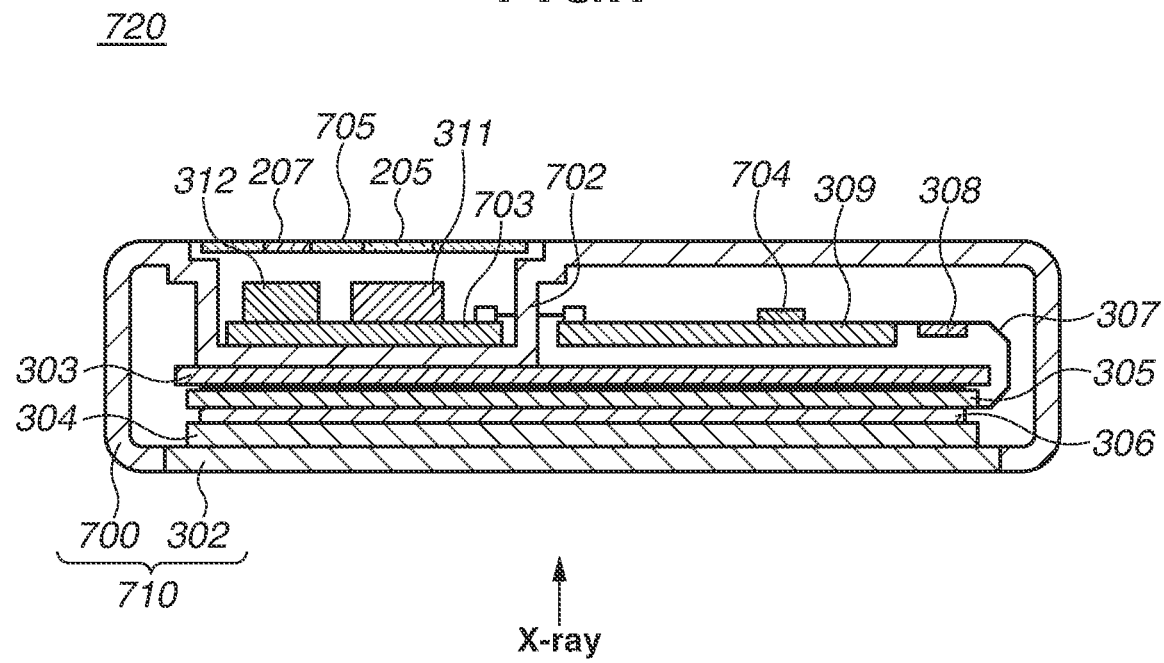
FIG. 7 is a cross-sectional view illustrating an arrangement of a sound transmission unit according to a third exemplary embodiment.

As illustrated in FIG. 7, in a third exemplary embodiment, the arrangement of a sound emitting member and a flexible substrate is defined.

An electrical signal read from the sensor panel 305 is weak and thus is susceptible to electromagnetic waves emitted from the sound emitting member 312. When the noise involved in the sound emission is superimposed on the electrical signal, the captured image can include noise or the false radiation detection can occur. Thus, the sound emitting member 312 is preferably arranged to emit the electromagnetic waves without affecting a circuit portion in charge of signal processing executed before the amplification and the AD conversion on the electrical signal. More specifically, the flexible substrate 307 through which the image signal and the radiation detection signal are transmitted to the electrical circuit board 309 is not preferably provided on the side of a casing 710 where the sound emitting member 312 is disposed. When the speaker unit is disposed on the rear surface of the casing 710, the flexible substrate 307 is not preferably provided to the side closest to the speaker unit. With the flexible substrate 307 and the sound emitting member 312 separated from each other by a predetermined distance, the negative impact of the electromagnetic waves from the sound emitting member 312 can be reduced.

The casing 710 has a wall 702 having a shielding property and provided between the sound emitting member 312 and an AD conversion unit 704. Thus, in the casing 710, the negative impact of the noise from the sound emitting member 312 on the sensor panel 305 can be reduced. More specifically, the wall 702 of the casing 710 is provided with an opening through which wiring, establishing connection between the electrical circuit board 309 on which the AD conversion unit 704 is mounted and an electrical circuit board 703 on which the sound emitting member 312 is mounted, passes through. The wall 702 can be integrated with the casing 710 or can be provided separately from the casing 710. For example, the casing 710 is partially recessed and the electrical circuit board 703 is provided inside the recess and outside the casing 710, whereas the electrical circuit board 309 is disposed inside the casing 710 so that the wall 702 of the casing 710 serves as a shielding wall. Thus, the noise on the AD conversion unit 704 due to the electromagnetic waves from the sound emitting member 312 can be reduced. The same applies to a configuration where the integrated circuit 308 performs the AD conversion. A detachable cover 705 can be attached to the recess.

Thus, the electrical circuit board 703 can be protected in the casing 710 and can be easily replaced. This function can be sufficiently achieved also with an imaging apparatus 720 having a configuration in which the electrical circuit board 703 is disposed inside the casing 710 and the electrical circuit board 309 on which the AD conversion unit 704 is mounted is disposed inside the recess and outside the casing 710. The imaging apparatus 720 can have a rib shaped wall formed on a plate member on the rear surface of the casing 710.

With the present exemplary embodiment, an imaging apparatus 720 can be obtained in which noise due to electromagnetic waves from a sound emitting member is reduced.

An imaging apparatus 200 according to a fourth exemplary embodiment is described with reference to FIG. 2 and FIG. 3. Description on contents in FIG. 2A and FIG. 3 that are similar to those in the first exemplary embodiment is omitted. FIG. 2B is a block diagram illustrating functional units of the imaging apparatus 200.

A volume control unit 208 controls the volume of the sound emitted from the sound transmission unit 207. The volume can be automatically or manually adjusted to be high or low, based on a reference volume level set in advance. In a configuration where the volume is automatically adjusted, the electrical circuit unit 202 sets the volume based on various types of information. Setting the volume includes setting a parameter with which the volume of the sound emitted from the sound transmission unit 207 is determined. Furthermore, the imaging control unit 120 can set the volume. In a configuration where the imaging control unit 120 sets the volume, the electrical circuit unit 202 is notified of information on the volume thus set through wired or wireless communications. Then, the volume control unit 208 controls the volume based on the volume information. In a configuration where the volume is manually adjusted, the imaging control unit 120 sets the volume based on an input from the operation unit 122. The reference volume level and the adjusted volume level are stored as appropriate. A storage unit 209 stores various parameters, used for controlling the imaging apparatus 200, as electronic data. For example, a parameter related to the volume level can be stored.

A control unit in the electrical circuit unit 202, the volume control unit 208, and another control unit, e.g., the imaging control unit 120, can cooperate to execute the processing related to the volume setting. Alternatively, a single control unit can be in charge of the processing. The control units can each be implemented with a CPU, a micro-processing unit (MPU), an FPGA, a Complex Programmable Logic Device (CPLD), or the like.

The present exemplary embodiment uses a detection unit that detects whether there is an approaching object (proximal object) in proximity to the sound transmission unit 207. In the present exemplary embodiment, the light emitting member 311 and the display unit 205 in FIG. 3 are respectively replaced with the detection unit and a through hole. The volume of the notification sound is automatically set based on a result of the detection.

The detection unit 311 includes, for example, a proximity sensor, an ultrasonic sensor, or an optical sensor, and detects an object outside of and in proximity to the imaging apparatus 200. A portion of the casing 330 facing the detection unit 311 includes the through hole 205. The sound transmission unit 207 and the through hole 205 are formed to be close to each other in the same surface of the casing 330, or are formed as an integrated hole. With such a configuration, the detection unit 311 can detect whether the through hole 205 is closed due to the installed environment, the orientation, and the like of the imaging apparatus 200. The volume control unit 208 sets the volume based on the result of the detection. When the through hole 205 is closed by an object external to and in proximity to the imaging apparatus 200, the sound transmission unit 207 disposed close to the through hole 205 is also likely to be closed. Thus, the notification is issued with a higher volume in a case where there is the proximal object (the through hole 205 is closed) than in a case where there is no proximal object (the through hole 205 is not closed).

The detection unit 311 can be a pressure sensor or the like directly formed on the casing 330. The pressure sensor can also be disposed in proximity to the sound transmission unit 207, so that the volume can be controlled based on a detected pressure value indicating whether the sound transmission unit 207 is closed.

Figure 9:
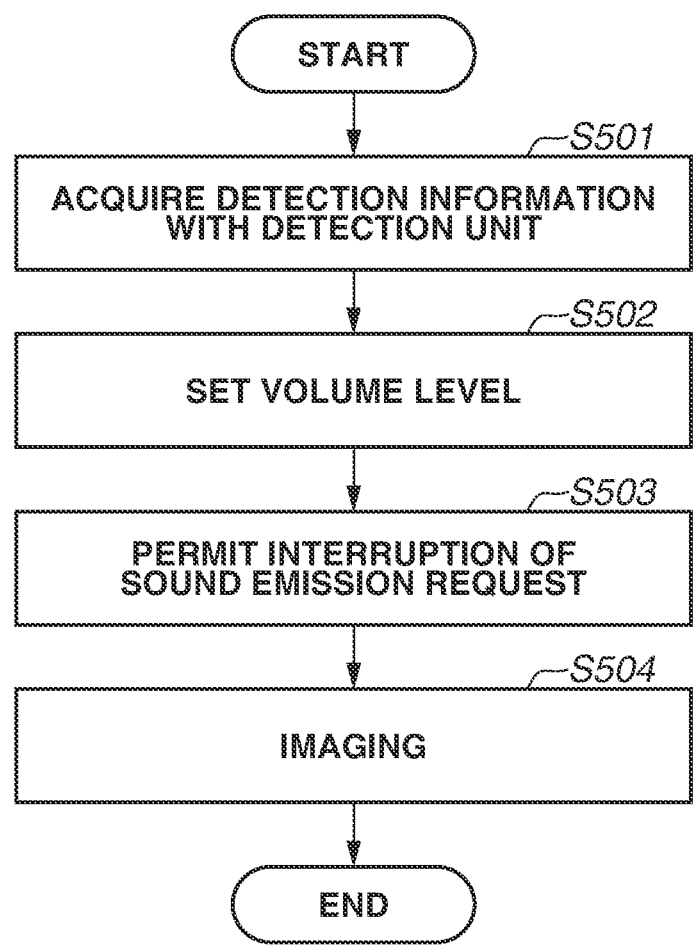
FIG. 9 is a flowchart illustrating imaging processing according to the fourth exemplary embodiment.

Next, a flow of processing executed by the imaging apparatus 200 is described with reference to FIG. 9. In the description below, the electrical circuit unit 202 sets the volume of the sound emitted from the sound transmission unit 207. The volume can also be set by the imaging control unit 120 or the other control unit as described above.

When the imaging apparatus 200 is booted, the electrical circuit unit 202 is booted by receiving power supply. The other components are also booted by receiving the power supply. In step S501, the electrical circuit unit 202 receives detection information from the detection unit 311, and transmits the detection information to the volume control unit 208. The detection information can be a value detected by a sensor of the detection unit 311, or can be information indicating whether there is a proximal object. When the value detected by the sensor is acquired as the detection information, the electrical circuit unit 202 can determine whether there is a proximal object.

In step S502, the electrical circuit unit 202 sets the volume level of the sound emitted from the sound emitting member 312 based on the detection information acquired in step S501. As described above, the volume for the notification is set to be higher in a case where the proximal object in proximity to the through hole 314 (thus, in proximity to the sound transmission unit 207) is detected than in a case where no proximal object is detected. When the imaging control unit 120 sets the volume, the detection information on the proximal object is received from the electrical circuit unit 202 through wired or wireless communications, and the information on the volume set based on the detection information is transmitted to the electrical circuit unit 202.

When the volume level is set in step S502, in step S503, the electrical circuit unit 202 permits interruption of a sound emission request. Thus, the volume control unit 208 performs control so that the sound emitting member 312 emits the sound based on the volume level set in step S502, whenever an interruption signal requesting for execution of sound emission is issued. In step S504, the electrical circuit unit 202 executes the imaging with the radiation emitted in accordance with an operation of the operator.

Figure 10:
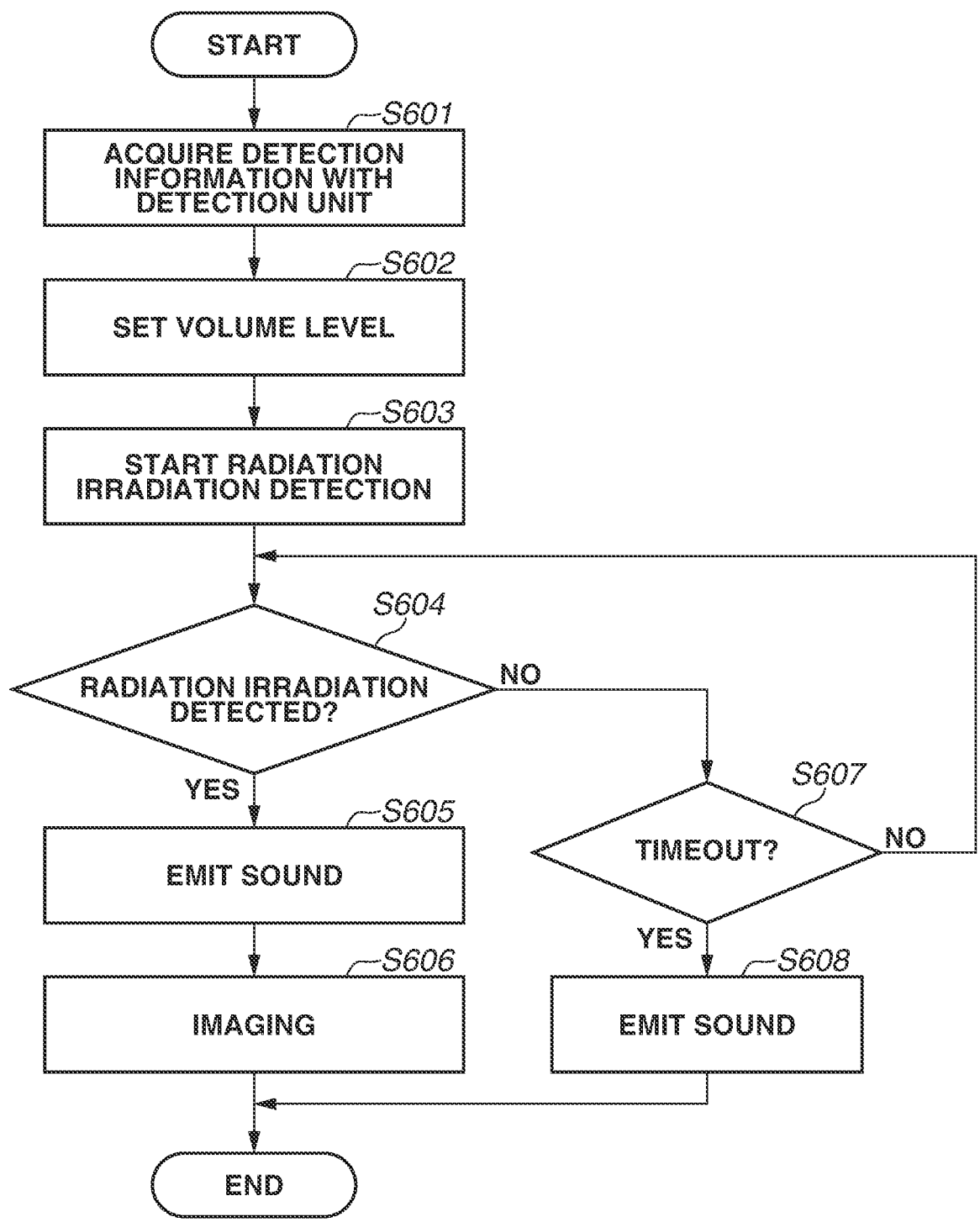
FIG. 10 is a flowchart illustrating another imaging processing according to the fourth exemplary embodiment.

Next, an example of processing of executing radiographic imaging with the radiation irradiation detection function is described with reference to FIG. 10. Processes in steps S601 and S602 are similar to those in steps S501 and S502 in FIG. 9.

In step S603, the electrical circuit unit 202 starts radiation irradiation detection in response to an input on the operation unit 122 by the operator. The functional units required for the radiation irradiation detection are energized to be booted before the detection starts. Notification indicating the start of the radiation irradiation detection can be issued using sound and light. When the radiation irradiation detection starts, the imaging apparatus 200 transitions to a radiation detection stand-by condition.

In step S604, the electrical circuit unit 202 determines whether the radiation irradiation is detected. When the radiation irradiation is detected (YES in step S604), the processing proceeds to step S605. When the radiation irradiation is not detected (NO in step S604), the processing proceeds to step S607.

In step S607, the electrical circuit unit 202 determines whether a predetermined time has elapsed after the radiation irradiation detection has started, that is, whether a detection time has expired (timeout). The detection time is set so that the radiation irradiation detection can be terminated when there is no radiation irradiation for a certain period of time. When the detection time has expired (YES in step S607), the processing proceeds to step S608. When the detection time has not yet expired (NO in step S607), the processing returns to step S604, and the radiation irradiation detection continues.

In step S608, the electrical circuit unit 202 causes the sound emitting member 312 to emit sound based on the volume level set in step S602 to issue notification indicating the timeout, and terminates the radiation irradiation detection. In FIG. 10, the notification is issued with sound when the detection time expires. Alternatively, the notification can be issued with sound when the remaining time until the timeout has reached a predetermined time.

When the radiation irradiation is detected in step S604 (YES in step S604), the processing proceeds to step S605. In step S605, the electrical circuit unit 202 causes the sound emitting member 312 to emit sound based on the volume level set in step S602 to issue notification indicating that the radiation irradiation is detected, and terminates the radiation irradiation detection. In step S606, the electrical circuit unit 202 executes the imaging.

In the present exemplary embodiment, the volume level is set immediately after the imaging apparatus 200 has booted. However, the time point of setting the volume level is not limited to this. In the configuration where the notification related to the radiation irradiation detection is issued with sound, for example, the volume level can be set when an instruction to transition to a mode for performing the radiation irradiation detection is issued by the operator before the radiation irradiation detection starts.

In a fifth exemplary embodiment, a configuration including an orientation detection unit that detects the orientation of an imaging apparatus is described. A configuration different from that in the fourth exemplary embodiment is mainly described, and the description on the similar configuration is omitted.

Figure 8:
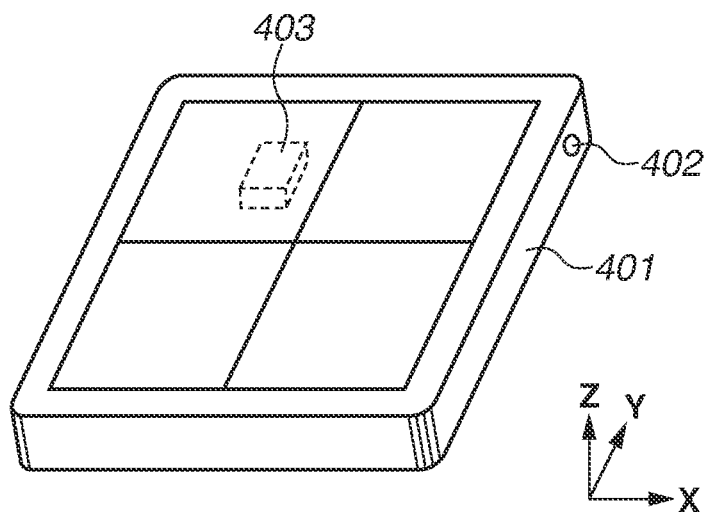
FIG. 8 is an outer view of a radiographic imaging apparatus according to a fifth exemplary embodiment.

FIG. 8 is a perspective view of an imaging apparatus 400 according to the present exemplary embodiment as viewed in a direction toward the radiation irradiation surface. The imaging apparatus 400 includes a casing 401 provided with a speaker unit 402. The speaker unit 402, which is provided on a side surface in the figure, can alternatively be provided on the rear surface. The imaging apparatus 400 incorporates an orientation detection unit 403. The orientation detection unit 403 includes a gyro sensor (angular velocity sensor) and the like for example, and detects the orientation of the imaging apparatus 400.

A positional relationship between three axes of the orientation detection unit 403 and the speaker unit 402 is registered in the storage unit 209 in advance. Thus, the volume of the sound emitted from the speaker unit 402 can be set in accordance with the orientation of the imaging apparatus 400 detected by the orientation detection unit 403. More specifically, the volume control unit 208 sets a high volume when the surface provided with the speaker unit 402 is determined to be a lower surface (faced down towards gravity) based on the positional relationship between the detected orientation of the imaging apparatus 400 and the speaker unit 402, because the sound is blocked to be small in this situation. The sound can be emitted based on any one of this volume setting using the orientation detection unit 403 and the volume setting according to the fourth exemplary embodiment or both.

The volume can also be set based on an imaging condition. For example, the volume is set to be higher when the imaging is executed with the surface, provided with the speaker unit 402, covered by an examinee taking a lying position. The volume is set to be low when the imaging is performed on a head, with an orientation in which the speaker unit 402 is not blocked. Thus, the volume can be more appropriately set based on a combination of a selected imaging condition and an orientation detected through orientation detection.

Figure 11:
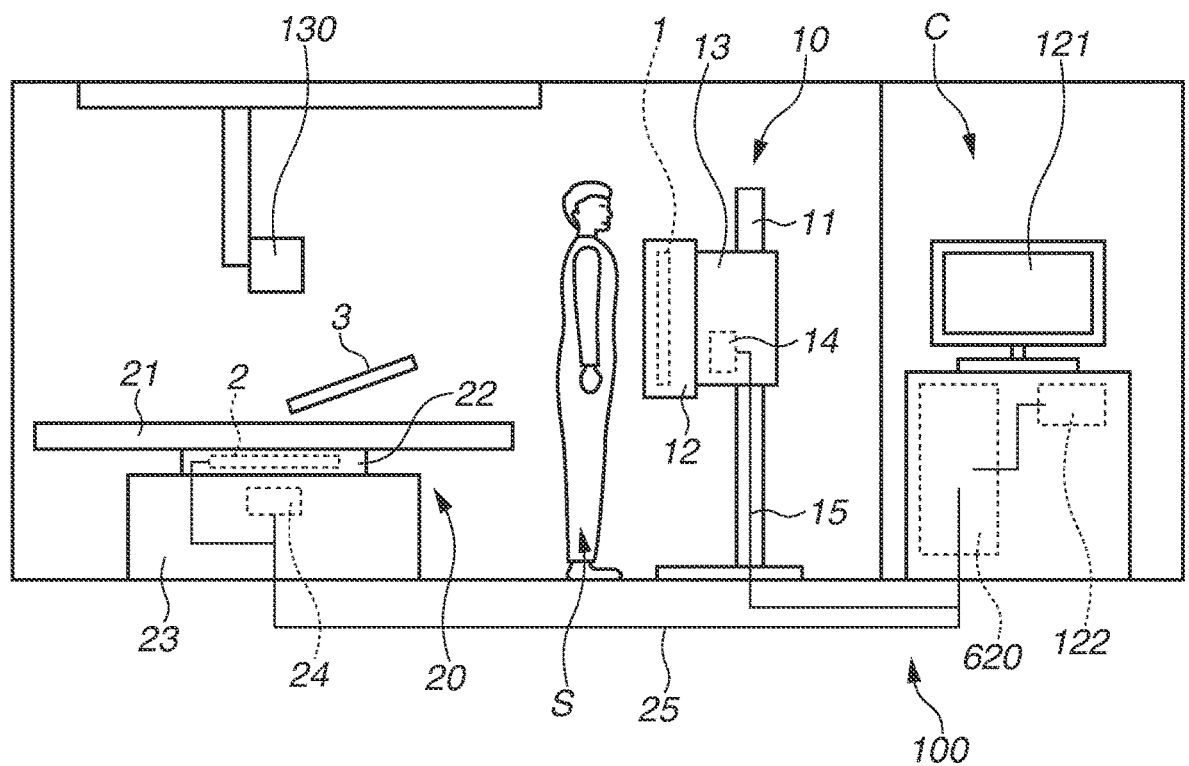
FIG. 11 is a schematic view of a radiographic imaging system according to a sixth exemplary embodiment.

FIG. 11 is a diagram illustrating a configuration of an imaging system 100 according to a sixth exemplary embodiment. Description on contents that are similar to those in the first exemplary embodiment is omitted. Imaging information according to the present exemplary embodiment is any one of information included in the examination order, information included in the imaging protocol, and information based on information in the examination order and/or the imaging protocol. Certain information included in the imaging information is referred to as imaging condition related information. In an example described in the present exemplary embodiment, the imaging condition related information is information related to an imaging portion of the subject.

A portion surrounded by an outer frame in FIG. 11 represents a radiation room (examination room). Components of the imaging system 100 are arranged at various locations in the radiation room, in accordance with their functions. The components are connected with each other through wired or wireless communications.

The imaging system 100 includes a radiation generation unit 130 and an imaging apparatus. The radiation generation unit 130 according to the present exemplary embodiment is an X-ray tube including a mechanism that changes the position, the orientation, and the posture, and irradiates a subject S with an X-ray.

Detection units 1, 2, and 3 each serve as the imaging apparatus. The detection unit detects electric charges corresponding to the amount of radiation transmitted through the subject S, generates a radiographic image (image data) based on the amount of electric charges, and outputs the radiographic image. FIG. 11 illustrates an example where a single room includes the three detection units. The number of detection units can be changed in accordance with the use and usability.

A standing position imaging apparatus 10 is mainly used when imaging the subject S in a standing position. The imaging is executed with the radiation reception surface of the detection unit 1 vertically arranged and the X-ray emitted in a substantially horizontal direction. The standing position imaging apparatus 10 includes a supporting column 11, a detection unit containing unit 12, a detection unit supporting unit 13, a standing imaging apparatus control unit 14, and a connection cable 15. The standing imaging apparatus control unit 14 performs control for adjusting a height of a supported position of the detection unit 1 in accordance with an imaging portion and a physical size of the subject S or the like, as well as the other like control. The standing imaging apparatus control unit 14 can be connected with the detection unit 1 to intermediate communications between the detection unit 1 and a processing unit 620. The connection cable 15 is an interface with which the detection unit 1 and the standing imaging apparatus control unit 14 are electrically connected to other components in the system.

A lying position imaging apparatus 20 is mainly used when imaging the subject S in a lying position. The imaging is executed with the detection unit 2 disposed to have the radiation reception surface horizontally arranged, and the X-ray emitted in a substantially vertical direction. The lying position imaging apparatus 20 includes a top plate 21, a detection unit containing unit 22, a base 23, a lying position imaging apparatus control unit 24, and a connection cable 25. The lying position imaging apparatus control unit 24 performs control for adjusting the height of the position of the top plate 21 in accordance with the imaging portion and the physical size of the subject S, as well as the other like control. The lying position imaging apparatus control unit 24 can be connected to the detection unit 2 to intermediate communications between the detection unit 2 and the processing unit 620 described below. The connection cable 25 is an interface with which the detection unit 2 and the lying position imaging apparatus control unit 24 are electrically connected to other components in the system.

The detection unit 3 is illustrated for purposes of describing an operation example where imaging is executed on an examinee taking a free position that is not restricted by any fixed tool. The imaging can be executed with the subject S and the detection unit 3 freely arranged without ruining the positional relationship relative to the radiation generation unit 103. The detection unit 3 can be connected to the processing unit 620 through wired communications via an electrical connection cable (not illustrated). Alternatively, a wireless communication function can be employed as described below to achieve higher convenience.

In many cases, a console C for operating the system is formed as a console room partitioned via a wall from a space where the imaging is executed on the subject S. The console C includes the processing unit 620, the display unit 121, and the operation unit 122. The processing unit 620 is, for example, a computer, and controls various operations and executes signal processing and image processing based on the imaging protocol by controlling the generation control unit 110 and the imaging control unit 120 in an interlocking manner. The processing unit 620 can have functions of the generation control unit 110 and the imaging control unit 120. The processing unit 620 is electrically connected to the standing position imaging apparatus 10 and the lying position imaging apparatus 20 respectively through the connection cables 15 and 25. The processing unit 620 can be combined with a relay device (not illustrated) having a wireless communication function to be capable of wirelessly communicating with the detection unit.

The console C is connected to a network (in-house network) external to the imaging system 100, and transmits and receives the examination order and an imaging (examination) result. The processing unit 620 can execute data processing on the examination order and the imaging protocol received from external to the imaging system 100, and transmit the examination order and the imaging protocol to the generation control unit 110 and the imaging control unit 120. The display unit 121 displays information such as a system state to the operator (radiographer). The display unit 121 is, for example, a computer display and can display the examination order received from external to the imaging system 100 or the examination order in the imaging system 100. The operation unit 122 receives an instruction from the operator. The operation unit 122 is a keyboard, a mouse, various buttons, or the like. The operator can use the operation unit 122 to input the imaging protocol based on the examination order and input an operation instruction to the detection unit.

Next, a flow of radiographic imaging on the subject S executed by the imaging system 100 is described. To execute the radiographic imaging on the subject S, the operator arranges the detection unit to be at a position to be irradiated with the radiation emitted from the radiation generation unit 103 and transmitted through the subject S. Next, the operator boots the detection unit, and then operates the operation unit 122 in the console C so that the detection unit transitions to the state where the imaging can be performed. Then, the operator operates the operation unit 122 to set an irradiation condition of the radiation to be emitted. When the operation described above is completed, the operator checks whether various preparations for the imaging, including that for the subject S, have been completed, and instructs the generation control unit 110 to emit the radiation by pressing an exposure switch on the operation unit 122.

Upon receiving this instruction for the radiation irradiation, the generation control unit 110 transmits a signal indicating start of the radiation irradiation to the detection unit. When the detection unit includes the radiation irradiation detection function, the generation control unit 110 does not to issue the radiation irradiation notification to the detection unit.

When the detection unit receives the signal indicating start of the radiation irradiation from the generation control unit 110, the detection unit checks whether the detection unit is prepared for the radiation irradiation. When the detection unit is prepared, the detection unit transmits irradiation permission to the generation control unit 110 as a response. Upon receiving the irradiation permission from the detection unit, the generation control unit 110 drives and thus causes the radiation generation unit 103 to emit the radiation. Upon detecting termination of radiation irradiation, the detection unit detects the electric charges corresponding to the amount of radiation transmitted through the subject S to start generating a radiographic image, and transmits the radiographic image thus generated to the console C. The termination of the radiation irradiation can be detected through various ways, including notification from the generation control unit 110 and detection of expiring of an irradiation time determined in advance. The processing unit 620 stores a radiographic image received from the detection unit in a storage medium, and displays the image on the display unit 121.

The detection unit according to the present exemplary is similar to that in the fourth exemplary embodiment described with reference to FIG. 2B, and thus will not be described.

FIG. 12 illustrates an example of a lookup table related to imaging condition and a parameter (hereinafter, referred to as a volume parameter) for determining the volume. The lookup table is stored in the storage unit 209. The lookup table can also be stored in the imaging control unit 120 or the console C. Storing the lookup table in the storage unit 209 of the detection unit (imaging apparatus) 200 is advantageous because such a configuration enables the lookup table to be read in the detection unit 200 even when communication is interrupted.

In FIG. 12, a left column includes imaging portions as an example an imaging condition and a right column includes volume parameters. In this example, the value of the volume parameter corresponds to the volume of sound emitted from the sound transmission unit 207. The volume control unit 208 controls the volume of the sound emitted from the sound transmission unit 207 based on the value of the volume parameter. As illustrated in FIG. 12, in the present exemplary embodiment, the volume parameter, that is, the volume from the sound transmission unit 207, is set to be lower for an imaging portion closer to the ears of the subject S (examinee). For example, the volume is set to be lower in a case where the imaging is executed on the subject's head close to the subject's ears than in a case where the imaging is executed on the subject's chest, abdomen, or the like.

Thus, the volume can be set in the following manner when an imaging portion A and an imaging portion B farther from the subject's ears than the imaging portion A are selectable. More specifically, the volume for the imaging executed on the imaging portion A is set to be lower than that for the imaging executed on the imaging portion B.

Figure 13:
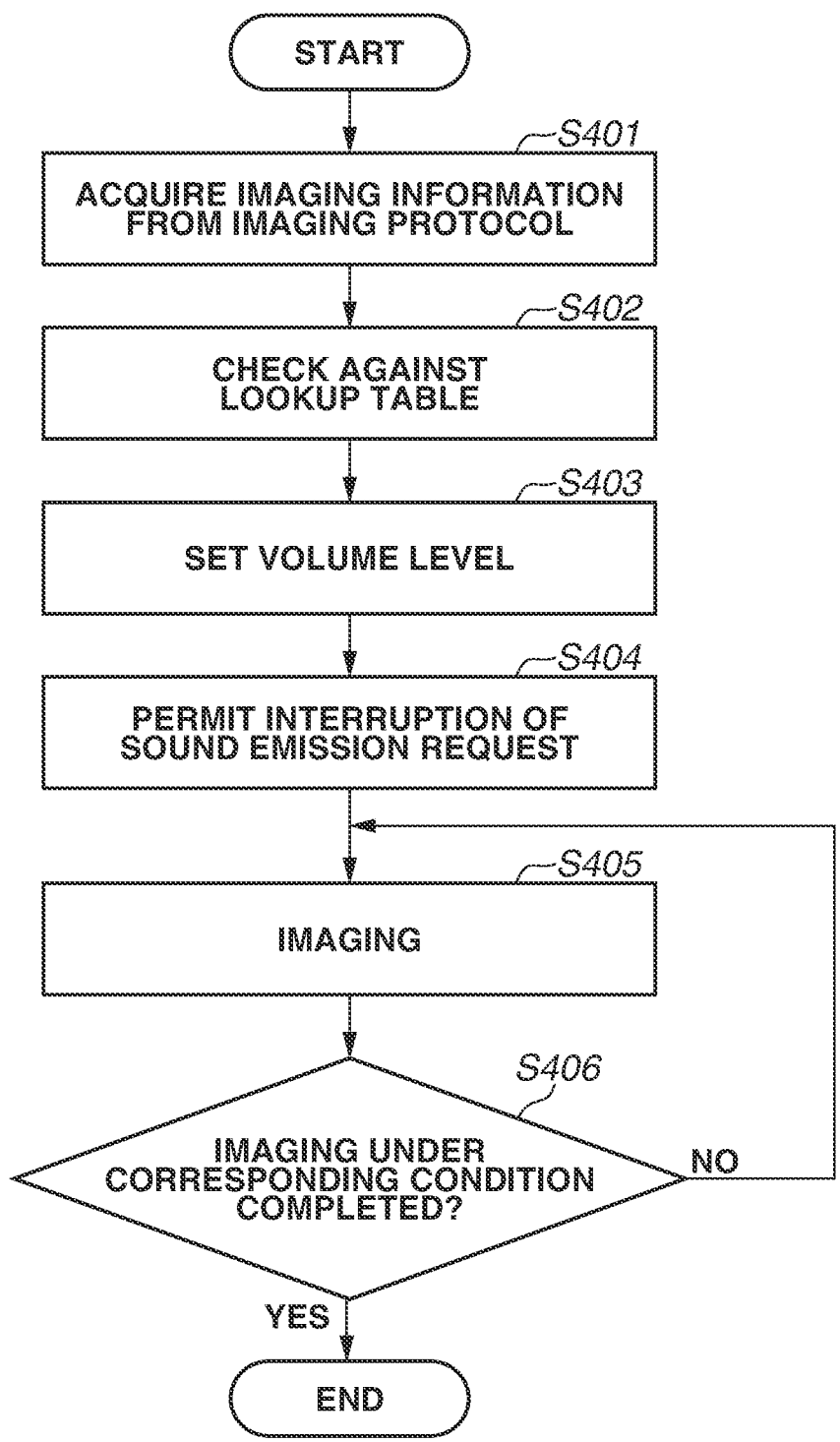
FIG. 13 is a flowchart illustrating imaging processing according to the sixth exemplary embodiment.

Next, a flow of imaging processing is described with reference to a flowchart in FIG. 13. A configuration where the electrical circuit unit 202 sets the volume of the sound transmission unit 207 is described below. Upon receiving the examination order that has been input, the imaging system 100 starts the imaging flow. In step S401, the electrical circuit unit 202 acquires the imaging information from the information on the imaging protocol issued as notification from the console C.

In step S402, the electrical circuit unit 202 checks the acquired information on the imaging portion against the lookup table stored in the storage unit 209. In step S403, the electrical circuit unit 202 acquires the information on the volume parameter corresponding to the imaging portion, and sets the volume level of the sound emitted from the sound transmission unit 207. The information on the volume parameter thus acquired is transmitted to the volume control unit 208. The lookup table can be stored in the console C, and the volume can be set in the console C (for example, by the processing unit 620). In such a configuration, the information on the volume parameter corresponding to the imaging portion is transmitted from the console C to the electrical circuit unit 202. The console C can acquire the information on the volume parameter corresponding to the imaging portion based on the examination information in the input examination order.

The above-described processing is completed before the imaging starts. In step S404, the electrical circuit unit 202 permits the interruption of the sound emission request. Thus, the volume control unit 208 performs control so that the sound is emitted from the sound transmission unit 207 based on the volume level set in step S403, whenever an interruption signal requesting for execution of sound emission is issued.

In step S405, the electrical circuit unit 202 executes the imaging with the radiation emitted based on an operation of the operator. When it is determined in step S406 that the imaging under an imaging condition (for example, an imaging portion) based on the imaging information acquired in step S401 has been completed (YES in step S406), the flow is terminated. A configuration can be employed in which the operator can manually adjust the volume level in detail, after the volume level has been automatically set through the above-described processing.

Figure 14:
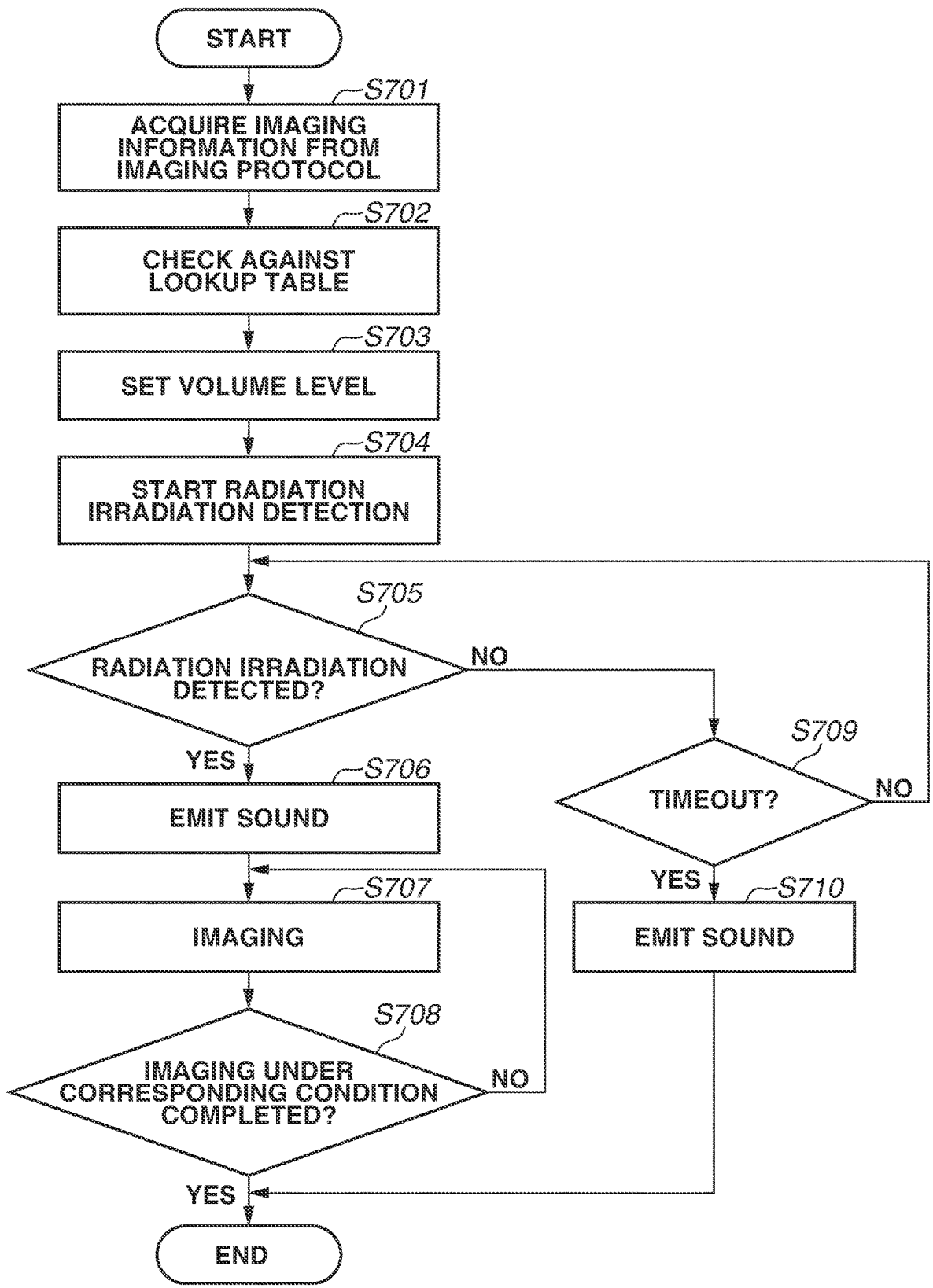
FIG. 14 is a flowchart illustrating another imaging processing according to the sixth exemplary embodiment.

A flow of imaging processing of performing radiographic imaging with the radiation irradiation detection function is described with reference to a flowchart in FIG. 14. Processes in steps S701 to S703 are similar to those in steps S401 to S403 in FIG. 13. The processing in steps S701 to S703 in FIG. 14 is executed before the radiation irradiation detection starts. For example, the volume level can be set when the operator issues an instruction to transition to the mode for performing the radiation irradiation detection.

In step S704, the electrical circuit unit 202 starts the radiation irradiation detection in response to an input on the operation unit 122 by the operator. The functional units required for the radiation irradiation detection are energized to be booted before the detection starts. Notification indicating the start of the radiation irradiation detection can be emitted using sound from the sound transmission unit 207. When the radiation irradiation detection starts, the imaging apparatus 200 transitions to the radiation detection stand-by condition.

In step S705, the electrical circuit unit 202 determines whether the radiation irradiation is detected. When the radiation irradiation is detected (YES in step S705), the processing proceeds to step S706. When the radiation irradiation is not detected (NO in step S705), the processing proceeds to step S709.

In step S709, the electrical circuit unit 202 determines whether a predetermined time has elapsed after the radiation irradiation detection has started, that is, whether a detection time has expired (timeout). The detection time is set so that the radiation irradiation detection can be terminated when there is no radiation irradiation for a certain period of time. When the detection time has expired (YES in step S709), the processing proceeds to step S710. When the detection time has not yet expired (NO in step S709), the processing returns to step S705, and the radiation irradiation detection continues.

In step S710, the electrical circuit unit 202 causes the sound transmission unit 207 to emit sound based on the volume level set in step S703 to issue notification indicating the timeout, and terminates the radiation irradiation detection. Here, the notification is issued with sound when the detection time expires. Alternatively, the notification can be issued with sound when the remaining time until the timeout reaches a predetermined time.

When the radiation irradiation is detected in step S705 (YES in step S705), the processing proceeds to step S706. In step S706, the electrical circuit unit 202 causes the sound transmission unit 207 to emit sound based on the volume level set in step S703 to issue notification indicating that the radiation irradiation is detected, and terminates the radiation irradiation detection. In step S707, the electrical circuit unit 202 executes the imaging. When it is determined in step S708 that the imaging for an imaging condition, e.g., an imaging portion, based on the imaging information acquired in step S701 has been completed (YES in step S708), the flow is terminated.

In a seventh exemplary embodiment, the volume of the notification sound is set based on information related to an imaging condition other than the imaging portion. A configuration different from that in the sixth exemplary embodiment is mainly described, and the description on the similar configuration is omitted.

As illustrated in FIG. 11, the detection unit, for example, can be used in an exposed state as in the case of the detection unit 3 in FIG. 11 or can be used while being contained in a container (hereinafter, referred to as a contained state). The standing position imaging apparatus 10 and the lying position imaging apparatus 20 are used with the detection units 1 and 2 respectively contained in the detection unit containing units (hereinafter, referred to as containing units) 12 and 22 each having a cover. In the contained state, the sound is less likely to reach the ears of the examinee than in the case where the detection unit is used in the exposed state. Thus, considering that the standing position imaging apparatus 10 and the lying position imaging apparatus 20, having the detection units contained in the containing units, are used, the volume is preferably set in accordance with the used condition of the detection unit.

FIG. 15 illustrates an example of a lookup table related to an imaging condition and a volume parameter. In the present exemplary embodiment, the volume of the sound transmission unit 207 is set based on the imaging condition by referring to the lookup table in FIG. 15, in step S402 in FIG. 13 and in step S702 in FIG. 14.

In FIG. 15, a left column includes imaging portions as an example an imaging condition and numerical values in the table indicates volume parameters for setting the volume level, as in FIG. 12. When the lookup table illustrated in FIG. 15 is used, the volume parameter is determined not only based on the imaging portion, but also based on the used condition of the detection unit (selected from three conditions P0, P1, and P2 in this example). The used conditions P0, P1, and P2 are selected as follows. More specifically, the condition P0 is selected when the detection unit 3 used in the exposed state is used, and the conditions P1 and P2 are each selected when a corresponding one of the detection units used in the contained state is used. In any of the conditions, the volume parameter is set to be smaller for a portion closer to the ears of the examinee, as in the sixth exemplary embodiment.

In the example illustrated in FIG. 15, the values of the volume parameters corresponding to the condition P0 are similar to those in FIG. 12, whereas larger values of volume parameters are set for the conditions P1 and P2. Thus, different volumes are set for the same imaging portion with the volume set to be higher in a case where the detection unit is used in the exposed state than in the case where the detection unit is used in the contained state. If the condition P1 corresponds to a state where the sound is easier to reach the ears than in the state corresponding to the condition P2, the value of the volume parameter under the condition P1 is set to be smaller than that under the condition P2, for the same imaging portion. It is to be noted that this relationship P0<P1<P2 regarding the volume needs not to be satisfied for all the imaging portions. For example, for the imaging portion sufficiently distant from the subject's ears, such as the lower body, the volume parameter under the condition P2 can be set to be the same as the volume parameters under the conditions P0 and P1. For example, the condition P1 or P2 can be selected in accordance with at least one of the thickness of the cover of the containing unit and the number and the size of openings of the standing position imaging apparatus 10, the lying position imaging apparatus 20, or the like to be used.

Any one of the conditions P0, P1, and P2, corresponding to different used states can be selected based on the information in the imaging protocol. For example, when the detection units are each used and/or contained in a fixed manner, the parameter can be selected based on information for designating the detection unit used for the imaging. The parameter can be selected based on information related to the posture of the subject during the imaging as an imaging target indicating whether the imaging is executed for the subject taking the standing position, the lying position, or the free position.

In the lookup table in FIG. 15, values of the volume parameters are preset in all the fields in the table. Alternatively, the volume parameters can be set in different manners. For example, the values can be preset for the volume parameters under only the condition P0, and the values of the volume parameters under the conditions P1 and P2 can be set through calculations. In such a case, for example, the volume parameters under the conditions P1 and P2 can be determined with a formula such as P1=P0+n, based on the preset value of the volume parameter P0 corresponding to the target imaging portion. In the example illustrated in FIG. 15, the highest value of the volume parameters is five, and conditional formulae for determining such a highest value as well as a minimum value or the like can also be set when the above-described formula is set.

The volume parameters and the formula are determined as appropriate through experiments and simulations based on a used condition of the apparatus. The parameter and the like can be selected through trials in an actual environment in the radiation room, and can be registered in the system by a staff that installs the apparatus or by the operator. For example, an editing function can be employed so that the values in the lookup table can be edited or another parameter column corresponding to a new used condition can be generated in addition to the condition P0. Thus, the parameters can be more appropriately adjusted in accordance with the situation.

The volume parameter can be set based on a condition other than the used condition of the detection unit. For example, when a relationship between a condition of the examinee, such as the age and health conditions, and how easy the sound can be heard can be identified, such a condition of the examinee can be used as the parameter of the imaging condition for preparing the lookup table of the volume parameters. In such a case, the information related to the condition of the examinee described above is acquired from the imaging protocol, and the volume level is set by checking this information against the lookup table.

At least one function of the above-described exemplary embodiments can be implemented by supplying a program to a system or an apparatus through a network or a storage medium, and reading and executing the program by at least one processor in a computer of the system or the apparatus. At least one function of the above-described exemplary embodiments can also be implemented with a circuit (for example, an application specific integrated circuit (ASIC)).

While exemplary embodiments have been described, it is to be understood that the disclosed exemplary embodiments are not seen to be limiting. The scope of the following claims is to be accorded the broadest interpretation to encompass all such modifications and equivalent structures and functions.

This application claims the benefit of Japanese Patent Applications No. 2016-196896, filed Oct. 5, 2016, No. 2016-228060, filed Nov. 24, 2016, and No. 2016-228062, filed Nov. 24, 2016, which are hereby incorporated by reference herein in their entirety.

What is claimed is:

1. A radiographic imaging apparatus comprising:
a sensor panel configured to convert radiation into an image signal;
a sound emitting member configured to provide notification of a state of the radiographic imaging apparatus via sound;
a casing configured to contain the sensor panel and the sound emitting member, the casing including a first sound transmission hole;
a sound transmission member configured to cover the first sound transmission hole, the sound transmission member including a second sound transmission hole with a smaller diameter than a diameter of the first sound transmission hole; and
a cover member configured to cover the first sound transmission hole from an outer side of the sound transmission member, the cover member including a third sound transmission hole.

2. The radiographic imaging apparatus according to claim 1, wherein the second sound transmission hole is disposed at a position facing the first sound transmission hole.

3. The radiographic imaging apparatus according to claim 1, wherein the second sound transmission hole includes a higher water stopping performance than the first sound transmission hole.

4. The radiographic imaging apparatus according to claim 1, wherein the sound transmission member includes one or more of water repellency and oil repellency.

5. The radiographic imaging apparatus according to claim 1, wherein the sound transmission member is fixed to an outer wall of the casing to cover the first sound transmission hole.

6. The radiographic imaging apparatus according to claim 1, wherein the third sound transmission hole has a diameter smaller than the diameter of the first sound transmission hole and larger than the diameter of the second sound transmission hole.

7. The radiographic imaging apparatus according to claim 1,
wherein the casing includes a plurality of first sound transmission holes, and
wherein the plurality of first sound transmission holes is provided at at least two surfaces of the casing.

8. The radiographic imaging apparatus according to claim 1, wherein the first sound transmission hole is located at a position recessed inward from an outermost shape of the casing.

9. The radiographic imaging apparatus according to claim 1, further comprising:
an integrated circuit configured to perform analog to digital conversion on a signal from the sensor panel; and
a flexible substrate configured to connect the integrated circuit and the sensor panel,
wherein a side surface of the casing closest to the sound transmission member and another side surface of the casing on which the flexible substrate is disposed are opposed to each other.

10. A radiographic imaging apparatus comprising:
a radiation detection unit configured to convert radiation transmitted through a subject into an electrical signal;
a sound emitting unit configured to emit sound for notification;
a detection unit configured to detect information related to an installed state of the radiographic imaging apparatus;
a control unit configured to control a volume of the emitted sound based on the detected information; and
a casing configured to contain the radiation detection unit,
wherein the detection unit is configured to detect at least one of information indicating whether there is an approaching object in proximity to the sound emitting unit, a pressure applied to the casing and information related to an orientation of the radiographic imaging apparatus.

11. The radiographic imaging apparatus according to claim 10, wherein the control unit is configured to perform control such that the volume of the emitted sound is set to be higher in a first installed state when the information indicates an approaching object is in proximity to the sound emitting unit than in a second installed state where the information indicates there is no approaching object in proximity to the sound emitting unit.

12. The radiographic imaging apparatus according to claim 10, wherein the detection unit is disposed in proximity to the sound emitting unit.

13. The radiographic imaging apparatus according to claim 10, wherein the detection unit includes one or more of a proximity sensor, an ultrasonic sensor, and an optical sensor.

14. The radiographic imaging apparatus according to claim 10, further comprising a casing configured to contain the radiation detection unit,
wherein the detection unit and the sound emitting unit are disposed on a same surface in the casing.

15. The radiographic imaging apparatus according to claim 14,
 wherein the sound emitting unit includes a sound emitting member,
 wherein the casing is provided with a sound transmission unit through which the sound emitted from the sound emitting member is output external to the radiographic imaging apparatus, and
 wherein the detection unit and the sound transmission unit are disposed in a same surface in the casing.

16. The radiographic imaging apparatus according to claim 10, further comprising a casing configured to contain the radiation detection unit,
 wherein the control unit is configured to perform control such that the volume of the emitted sound is set to be higher in a case where a surface in the casing on which the sound emitting unit is disposed faces a predetermined direction than in a case where the surface does not face the predetermined direction.

17. The radiographic imaging apparatus according to claim 16, wherein information indicating a relationship between the detected information and a position where the sound emitting unit is disposed is stored in advance.

18. The radiographic imaging apparatus according to claim 16, wherein the predetermined direction is downward towards gravity.

19. The radiographic imaging apparatus according to claim 10, wherein the control unit is configured to acquire information related to an imaging condition, and to control the volume of the emitted sound based on a combination of the information related to the imaging condition and information related to the orientation of the radiographic imaging apparatus.

20. The radiographic imaging apparatus according to claim 10, further comprising an irradiation detection unit configured to detect radiation irradiation,
 wherein the control unit is configured to set the volume of the emitted sound before the irradiation detection unit starts the radiation irradiation detection.

21. The radiographic imaging apparatus according to claim 20, wherein the sound emitting unit provides notification that the irradiation detection unit has detected radiation irradiation.

22. The radiographic imaging apparatus according to claim 20, wherein the sound emitting unit provides notification that a predetermined time has elapsed after the irradiation detection unit started an operation of detecting the radiation irradiation.

23. A radiographic imaging system comprising:
 a radiographic imaging apparatus including a radiation detection unit configured to convert radiation transmitted through a subject into an electrical signal and a sound emitting unit configured to emit sound for notification;
 an acquisition unit configured to acquire information related to an imaging condition; and
 a setting unit configured to set a volume of the emitted sound based on the information related to the imaging condition.

24. The radiographic imaging system according to claim 23, wherein first information indicating a correspondence relationship between the imaging condition and information related to the volume of the emitted sound is pre-stored.

25. The radiographic imaging system according to claim 24,
 wherein the setting unit is configured to acquire, based on the information related to the imaging condition, the information related to the volume corresponding to the imaging condition from the first information, and
 wherein the emitted sound is emitted with a volume based on the information related to the acquired information related to the volume.

26. The radiographic imaging system according to claim 25, wherein the setting unit is configured to set the volume of the emitted sound to be lower in a case where an imaging portion is a first portion than in a case where the imaging portion is a second portion that is a portion farther from a subject's ears than the first portion is.

27. The radiographic imaging system according to claim 26,
 wherein the first portion is a portion including a subject's head, and
 wherein the second portion is a portion different from the subject's head.

28. The radiographic imaging system according to claim 27, wherein the information related to the imaging condition includes information related to a use state of the radiographic imaging apparatus.

29. The radiographic imaging system according to claim 28, wherein the setting unit is configured to set, for at least one imaging portion, the volume of the emitted sound to be lower in a case where the radiographic imaging apparatus is used in a non-contained state than in a case where the radiographic imaging apparatus is used in a contained state.

30. The radiographic imaging system according to claim 28, wherein the information related to the use state of the radiographic imaging apparatus is determined based on information for specifying radiographic imaging apparatuses to be used for imaging.

31. The radiographic imaging system according to claim 28, wherein the information related to the use state of the radiographic imaging apparatus is determined based on information related to a posture of a subject during imaging.

32. The radiographic imaging system according to claim 23, further comprising a processing device configured to receive an examination order from external to the radiographic imaging system and an imaging protocol defining a parameter related to an imaging,
 wherein the acquisition unit is configured to acquire the information related to the imaging condition based on the examination order or the imaging protocol.

33. A radiographic imaging apparatus comprising:
 a radiation detection unit configured to convert radiation transmitted through a subject into an electrical signal;
 a sound emitting unit configured to emit sound for notification;
 an acquisition unit configured to acquire information related to an imaging condition; and
 a setting unit configured set a volume of the emitted sound based on the information related to the imaging condition.

* * * * *